United States Patent
Ganey

(10) Patent No.: US 10,874,765 B2
(45) Date of Patent: Dec. 29, 2020

(54) APPARATUSES AND METHODS FOR PRODUCING ENRICHED FIBRILLATED TISSUE MATRICES

(71) Applicant: Timothy Ganey, Tampa, FL (US)

(72) Inventor: Timothy Ganey, Tampa, FL (US)

(73) Assignee: JUPITER BIOLOGICS, LLC, Tulsa, OK (US)

( * ) Notice: Subject to any disclaimer, the term of this patent is extended or adjusted under 35 U.S.C. 154(b) by 0 days.

(21) Appl. No.: 16/409,934

(22) Filed: May 13, 2019

(65) Prior Publication Data
US 2019/0262503 A1     Aug. 29, 2019

Related U.S. Application Data

(62) Division of application No. 16/034,487, filed on Jul. 13, 2018, now Pat. No. 10,286,109.

(60) Provisional application No. 62/533,648, filed on Jul. 17, 2017.

(51) Int. Cl.
*A61L 27/36*     (2006.01)
*A61L 27/54*     (2006.01)

(52) U.S. Cl.
CPC ........... *A61L 27/3691* (2013.01); *A61L 27/36* (2013.01); *A61L 27/54* (2013.01); *A61L 2300/414* (2013.01); *A61L 2300/426* (2013.01)

(58) Field of Classification Search
CPC ....... A61L 27/36; A61L 27/54; A61L 27/3691
See application file for complete search history.

(56) References Cited

FOREIGN PATENT DOCUMENTS

WO    WO 2016/207523    12/2016

OTHER PUBLICATIONS

Derwent Abstract for CN 101880331 A, Inventor: Hu et al. (Year: 2010).*
Nam Kwangwoo et al. Fabrication of a heterostructural fibrillated collagen matrix for teh regeneration of soft tissue function. Soft Matter, 2012, 8, pp. 472-480.
Magno Valentia et al. Macromolecular crowding for tailoring tissue-derived fibrillated matrices. Acta Biomaterialia, Apr. 2017, pp. 1-34.
Huang An et al. Fabrication of poly(3-caprolactone) tissue engineering scaffolds with fibrillated and interconnected pores utilizing microcellular injection molding and polymer leaching. RSC Advances, 2017, 7, pp. 43432-43444.
PCT/US18/42290 Notification of transmittal of the international search report and the written opinion of the international searching authority, or the declaration dated Nov. 1, 2018.
PCT/US18/42290 International search report dated Nov. 1, 2018.
PCT/US18/42290 Written opinion of the international searching authority dated Nov. 1, 2018.

* cited by examiner

*Primary Examiner* — Sean E Conley
(74) *Attorney, Agent, or Firm* — John M. Behles

(57) ABSTRACT

Apparatuses and methods for producing enriched fibrillated tissue matrices are disclosed herein. Some embodiments include a method including subjecting tissue in a carrier liquid to a fibrillation pressure while maintaining a temperature of the tissue and the carrier liquid to at or below a safe zone temperature; inducing a phasic shift and rapid release of water and biological components from the tissue through a disruptive boil and tissue explosion process to produce a fibrillated tissue matrix; and recapturing the water and biological components.

17 Claims, 6 Drawing Sheets

APPARATUSES AND METHODS FOR PRODUCING ENRICHED FIBRILLATED TISSUE MATRICES

CROSS REFERENCE TO RELATED APPLICATIONS

This application is a divisional of U.S. patent application Ser. No. 16/034,487, titled "APPARATUSES AND METHODS FOR PRODUCING ENRICHED FIBRILLATED TISSUE MATRICES", filed on Jul. 13, 2018, which claims the benefit and priority of United States Provisional Application Ser. No. 62/533,648, titled "APPARATUSES AND METHODS FOR PRODUCING ENRICHED FIBRILLATED TISSUE MATRICES", filed on Jul. 17, 2017, each of which are hereby incorporated by reference herein in their entireties including all references and appendices cited therein, for all purposes.

FIELD OF THE INVENTION

The present disclosure is directed generally, in some embodiments, to the preparation of fibrillated tissue matrices, and more specifically, but not by limitation to apparatuses and methods for producing fibrillated tissue for use in medical treatments such as tissue allograft procedures.

SUMMARY

According to some embodiments, the present disclosure is directed to a method comprising placing a carrier liquid into a pressure vessel, introducing tissue into the carrier liquid, pressurizing the carrier liquid and the liquid within the pressure vessel to a critical pressure, selectively controlling a temperature of within the pressure vessel so as to preserve biological components of the tissue during a boiled liquid expanding vapor explosion (BLEVE) process, and depressurizing the pressure vessel to trigger the BLEVE process to produce a fibrillated tissue matrix and a vaporized fluid comprising at least a portion of the biological components. In the full sense of the application, or to better define "boil" in the context of this disclosure, the embodiment defines a method to change from a liquid to a gaseous state, producing bubbles of gas that rise to the surface of the liquid, agitating it as they rise, with temperature a balanced equilibrium of pressure to attain those results.

According to some embodiments, the present disclosure is directed to a method comprising subjecting tissue in a carrier liquid to a fibrillation pressure while maintaining a temperature of the tissue and the carrier liquid to at or below a safe zone temperature; inducing a phasic shift and rapid release of water and biological components from the tissue through a disruptive boil and tissue explosion process to produce a fibrillated tissue matrix; and recapturing the water and biological components.

According to some embodiments, the present disclosure is directed to a system/apparatus comprising a pressure vessel that can be selectively controlled with a control system relative to pressure and temperature to fibrillate a tissue disposed inside the pressure vessel, the tissue being disposed in a carrier fluid, the tissue being fibrillated using boiled liquid expanding vapor explosion (BLEVE) through pressurization of the pressure vessel and rapid decompression of the pressure vessel, the temperature within the pressure vessel being controlled so as to preserve biological components of the tissue during BLEVE, and reclaim for recombination and subsequent lyophyilization as an intact whole material in a form of a fibrillated tissue matrix that results from pressure modified processing with dehydration as a summative final difference.

BRIEF DESCRIPTION OF THE DRAWINGS

Certain embodiments of the present technology are illustrated by the accompanying figures. It will be understood that the figures are not necessarily to scale and that details not necessary for an understanding of the technology or that render other details difficult to perceive may be omitted. It will be understood that the technology is not necessarily limited to the particular embodiments illustrated herein.

DESCRIPTION OF EXEMPLARY EMBODIMENTS

Generally speaking, the present disclosure is directed to apparatuses and methods for producing fibrillated tissue matrices. Example methods comprise any combination or permutation of tissue fibrillation, matrix recombination, and lypholization—just to name a few. The resultant enriched, fibrillated tissue matrices are exosome rich and cytokine rich, and can be used in medical procedures such as cartilage allograft procedures.

In some embodiments, fibrillated tissue is created using a pressure vessel apparatus. Tissue segments are placed into the pressure vessel apparatus and the pressure vessel apparatus is at least partially filled with a carrier fluid. The pressure vessel apparatus is configured in some embodiments to pressurize its contents while maintaining a temperature of the contents approximately within a safe zone temperature range. The maintenance of the contents of the pressure vessel at the safe zone temperature range reduces a likelihood of deleterious damage to tissue components such as exosomes, cytokines, growth factors, sulfated proteoglycans, and other similar tissue components that might result from an increase in temperature when a corresponding increase in pressure within the pressure vessel apparatus is achieved. That is, the pressure vessel apparatus comprises a cooling means that offsets a corresponding increase in temperature within the pressure vessel due to increased pressure in the pressure vessel apparatus.

When the pressure vessel apparatus has been pressurized to a fibrillating pressure, the pressure inside the pressure vessel apparatus is rapidly released causing the tissue segments to fibrillate in a process known as boiled liquid expanding vapor explosion ("BLEVE").

In one or more embodiments, cartilage (or any tissue) and suitable carrier such as saline are combined into a thick-wall pressure vessel that can be highly pressurized and safely contained. Pressure is increased in the vessel up to a desire fibrillation pressure. Once the fibrillation pressure has been achieved, pressure is rapidly reduced, resulting in a phasic shift and rapid release of water from the tissue through a disruptive boil and tissue explosion.

Figure 1:
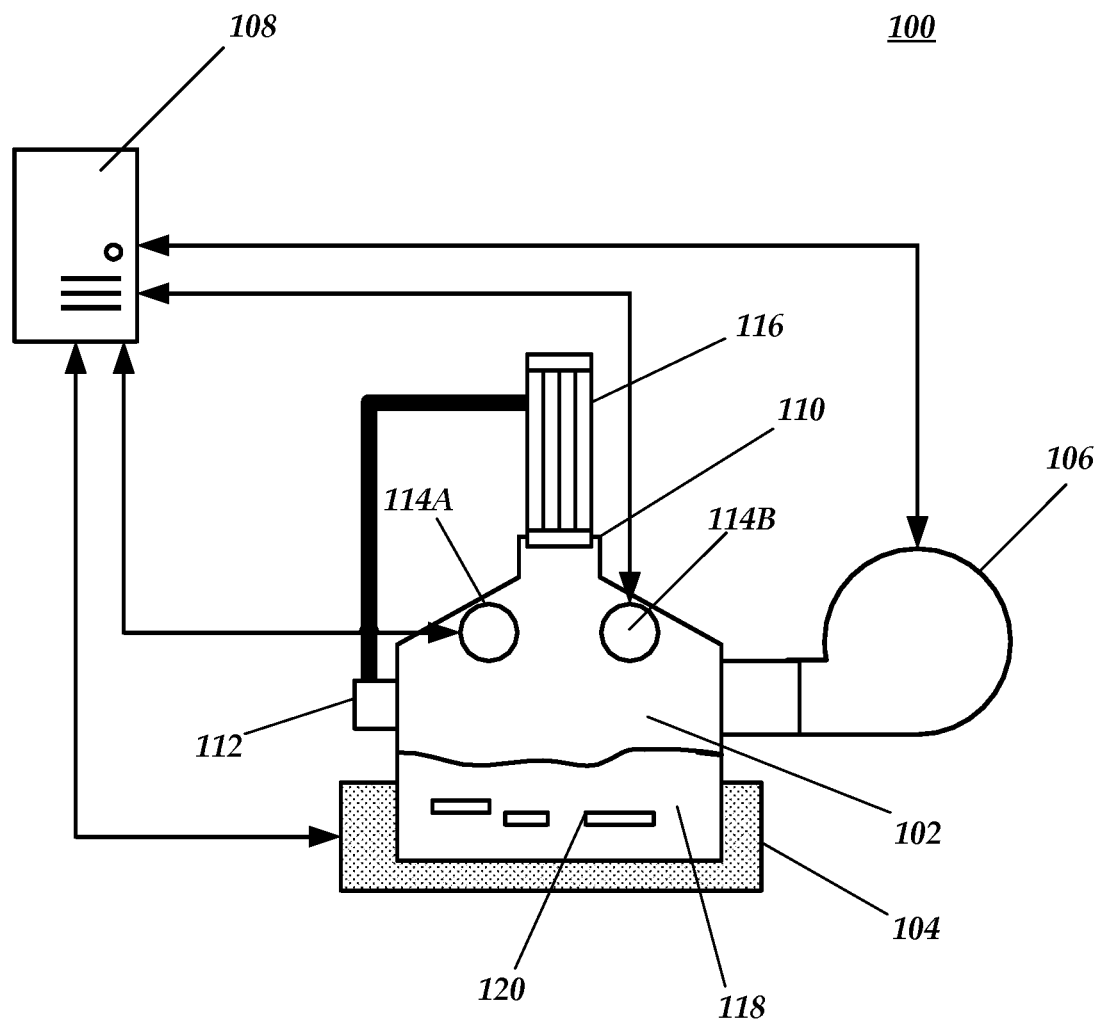
FIG. 1 is a schematic diagram of a system of the present disclosure.

FIG. 1 is a schematic view of an example pressure vessel apparatus constructed in accordance with the present disclosure. The pressure vessel apparatus 100 comprises a pressure vessel 102, a cooling assembly 104, a pump 106, and a control system 108. Additional or fewer components than those illustrated can be utilized as would be apparent to one of ordinary skill in the art with the present disclosure before them.

In some embodiments, the pressure vessel 102 comprises a thick-wall vessel of any shape and/or size, constrained by design and/or manufacturing constraints, such as tissue and carrier fluid processing volume. The pressure vessel 102 can be manufactured from any suitable material such as stainless steel, although other materials that would be known to one of ordinary skill in the art with the present disclosure before them are likewise contemplated for use in accordance with the present disclosure.

The pressure vessel 102 comprises a port 110 that allows for either or both of inputting of tissue segments and carrier fluid and/or discharging of fibrillated tissue matrices. In some embodiments, the port 110 can function as a one-way valve that allows fibrillated tissue to be discharged when a pressure in the pressure vessel 102 reaches approximately a fibrillating pressure. In another embodiment, the port 110 is an actuated valve that opens under control from the control system 108.

The tissue segments and carrier fluid can be introduced through another input port, such as secondary port 112, or by any other means that would be known to one of ordinary skill in the art. The secondary port 112 can also couple with a condenser as described below, which will reintroduce condensed vaporized biological components back into the pressure vessel 102, in some embodiments. The respective use of the port 110 or secondary port 112 for introduction or release of materials is based on design choice as would be appreciated by one of ordinary skill in the art with the present disclosure before them.

The cooling assembly 104 is in fluid communication with the pressure vessel 102. The cooling assembly 104 can comprise any suitable cooling means that allows a temperature within the pressure vessel 102 to be regulated. This could include liquid heat transfer where the pressure vessel 102 is in contact with a cooling fluid of the cooling assembly 104. Another example would comprise the use of a coiled tube heat exchanger coil wrapped around the pressure vessel 102. In one or more embodiments a means for cooling can be integrated into the pressure vessel 102 itself.

In some embodiments, the pump 106 is utilized to increase a pressure within the pressure vessel 102. The pump 106 can pressurize the pressure vessel 102 with any fluid, such as air, although other fluids that enhance tissue component extraction and/or preservation can also be utilized. In one or more embodiments, the carrier fluid can comprise, for example, nitric oxide, which has a relatively short half-life and is materially advantageous to cells and vascular tissue for dilation and flow of metabolites. The use of nitric oxide provides biological advantages and enhancements relative to saline.

The control system 108 can comprise any computing system, such as a server or specific-purpose (e.g., specifically programmed) computing system. The control system 108 can comprise computing components such as a processor, memory, display and other related components that would be known in the art. The memory stores executable instructions and logic for storing, for example, algorithms that control the pressure within the pressure vessel 102 and the temperature within the pressure vessel 102. Thus, the control system 108 can comprise one or more sensors (such as a pressure sensor 114A and a temperature sensor 114B) that are associated with the pressure vessel 102 and are configured to monitor any of pressure and temperature inside the pressure vessel 102. The processor can execute the instructions stored in memory to control operations of the pressure vessel 102 to fibrillate the tissue segments according to the present disclosure.

In one embodiment, the control system 108 continuously monitors the pressure and temperature within the pressure vessel 102 allowing a pressure within the pressure vessel 102 to reach approximately at or above a fibrillating pressure within the pressure vessel 102, while simultaneously maintaining a temperature within the pressure vessel 102 at a desired temperature range. Example pressures that can be used include placing the tissue segments at, near, or approximately above a critical pressure, which would induce a phase change through the use of BLEVE. Example operating temperatures would be between zero and 100 degrees Celsius, inclusive. In one or more embodiments, the temperature within the pressure vessel is brought as low as possible while allowing pressure inside the pressure vessel to increase to a point at which BLEVE can occur by decompression. In other embodiments, pressures ranging from approximately 300-600 MPa, inclusive and from approximately 100-400 MPa, inclusive are contemplated for use.

Thus, the control system 108 can either directly or indirectly control the pump 106 and cooling assembly 104 to ensure that the pressure and temperature are within desired operating ranges. For example, if the pressure increases causes unexpected increases in temperature, the control system 108 can reduce the pressure or the cooling assembly 104 can be controlled to reduce the temperature to a desired ranges.

When pressure inside the pressure vessel 102 reaches the fibrillating pressure, the control system 108 opens the port 110, rapidly decompressing the pressure vessel 102 and causing BLEVE of the tissue segments to fibrillate the tissue segments. During fibrillation, biological constituent parts within the tissue segments separated and captured. The fibrillated matrix is a desiccated residual matrix, while the biological constituent parts such as exosomes, cytokines, growth factors, sulfated proteoglycans, and other similar tissue components, separate from the fibrillated matrix and are vaporized in the BLEVE process. In some embodiments, the boiled/vaporized fluid can be condensed in a condenser 116, allowing the biological constituent parts to return to a liquid form and enter the carrier liquid. This evaporative/condensing process results in the capture of a biological constituent distillate that is rich in exosomes, cytokines, growth factors, sulfated proteoglycans, and other similar tissue components.

According to some embodiments, the desiccated, fibrillated matrix is reconstituted by combining the matrix with the enriched distillate to produce an enriched fibrillated matrix that has been enriched in concentration relative to the native, but reformulated to a matrix with increased surface areas, greater porosity, and more plastic conformation.

In sum, the process creates an infiltrable matrix (e.g., fibrillated tissue matrix), that has been replenished with its natural biologic constituents, and in the process enhances surface area, enriches exchange of biological fluids, and accelerates integration when implanted.

The concepts disclosed herein can be utilized in combination with other systems. For example, a fibrillated product produced that has been reconstituted in accordance with the present disclosure can be used as an allograft. Prior to use, this allograft can be placed in a centrifuge along with patient specific protein rich platelets (PRP) and spun at a sufficient rate to pellet and flatten the matrix. This process also further enriches the matrix with patient specific cells, cell products, and cytokines that are native to the host, so as to produce a chimeric graft that is matrix allograft and cytokine autologous.

In operation, a carrier fluid 118, such as a saline solution is introduced into the pressure vessel 102. Next, tissue segments 120 are introduced into the carrier fluid 118. This could comprise, for example, shavings of a tissue such as cartilage. The control system 108 controls the pump 106 to increase pressure within the pressure vessel 102. The temperature and pressure sensors (e.g., one or more sensors 114A and 114B) are used to allow the control system 108 to continuously monitor pressure and temperature within the pressure vessel 102. As the pressure increases a corresponding increase in temperature begins. The control system 108 then controls the cooling assembly 104 to control the temperature within the pressure vessel 102 to within a desired temperature range. In some embodiments, this range comprises a physiologic range comprising between approximately 35-41 degrees Centigrade, inclusive, to take advantage of pyrogenic cytokines and their effective activity on cell shedding and reaction during the preparation and extraction phases.

Again, this temperature range allows for preservation of biological components such exosomes and growth factors in the tissue segments 120 that might otherwise be deleteriously damaged by high temperature within the pressure vessel 102. Once a fibrillating pressure is reached within the pressure vessel 102, the control system 108 can activate the port 110 to open causing a rapid decompression within the pressure vessel 102 to cause BLEVE, which in turn converts the tissue segments 120 into a fibrillated matrix. This fibrillated matrix is dehydrated during the BLEVE process when water and biological components are separated from the fibrillated matrix.

In some embodiments the biological components of the tissue segments 120 and carrier fluid 118 that are vaporized during BLEVE are condensed using the condenser 116. This condensate (e.g., enriched carrier fluid) is then pumped or otherwise delivered back into the pressure vessel 102 or any other suitable container to create an enriched carrier fluid. That is, the biological components of the tissue segments that separate from the fibrillated matrix during BLEVE will condense back into the carrier fluid. This enhanced carrier fluid can be used to reconstitute the fibrillated matrix to produce an enriched fibrillated matrix that is ready for use in any number of medical procedures or to create implantable objects.

In one embodiment, the enriched carrier fluid (e.g., biological constituent distillate) is captured and reused at a later time to rehydrate the dehydrated, fibrillated tissue matrix, such as any suitable time prior to using the fibrillated matrix in a patient. The enriched carrier fluid can be stored in a pharmaceutically acceptable manner until required for rehydration of the dehydrated, fibrillated tissue matrix.

By way of non-limiting example, the fibrillated matrix and/or enriched fibrillated matrix can be used to create a cartilage allograft used to for grafting into a patient. In some embodiments, additional compounds can be introduced into the fibrillated matrix such as a tissue growth enhancing product, a medicament such as an anti-rejection preparation, a filler, or any combinations thereof.

In sum, the pressure vessel apparatus 100 includes a pressure vessel that can be selectively controlled with a control system relative to pressure and temperature to fibrillate a tissue disposed inside the pressure vessel. In various embodiments the tissue is disposed in a carrier fluid and the tissue being fibrillated using boiled liquid expanding vapor explosion (BLEVE) through pressurization of the pressure vessel and rapid decompression of the pressure vessel. In one or more embodiments the temperature within the pressure vessel is controlled so as to preserve biological components of the tissue during BLEVE, and reclaim for recombination and subsequent lyophyilization as an intact whole material in a form of a fibrillated tissue matrix that results from pressure modified processing with dehydration as a summative final difference.

FIG. 2 is a flowchart of an example method of the present disclosure. The method includes a step 202 of placing a carrier liquid into a pressure vessel. This can include introducing saline or another biologically compatible (suitable for use in vivo in a patient) liquid into a pressure vessel.

Next, the method includes a step 204 of introducing tissue into the carrier liquid. This can include placing particulate preparations of the tissue (of any size desired depending on the application) such as shavings, into the carrier liquid. In some instances, steps 202-204 are combined such that the tissue is mixed into the carrier liquid prior to introduction into the pressure vessel.

In various embodiments, the method includes a step 206 of pressurizing the carrier liquid and the liquid within the pressure vessel to a critical pressure. Example pressures for the pressure vessel are disclosed supra. In combination with step 206, the method includes a step 208 of selectively controlling a temperature of within the pressure vessel so as to preserve biological components of the tissue during a boiled liquid expanding vapor explosion (BLEVE) process. As noted throughout, the temperature can be controlled by an temperature controlling means desired that will allow the contents of the pressure vessel to remain at approximately zero to 100 degrees Celsius during pressurization.

In one or more embodiments, the method includes a step 210 of depressurizing the pressure vessel to trigger the BLEVE process to produce a fibrillated tissue matrix and a vaporized fluid comprising at least a portion of the biological components. This can be accomplished by releasing a valve on the pressure vessel such that a decompression occurs that is sufficient to trigger BLEVE.

The method of FIG. 2 can further comprise an optional sub-method (illustrated in dotted line) for capturing enriched carrier fluid. The sub-method includes a step 212 capturing the vaporized fluid using, for example, a condenser, and a step 214 of condensing the vaporized fluid into a biological constituent distillate. The biological constituent distillate includes the carrier fluid plus any liquid or particulate biological components liberated from the tissue or otherwise produced during BLEVE.

FIG. 3 is another example method of the present disclosure that reflects the use of a fibrillated tissue matrix produced in the method of FIG. 2. The method of FIG. 3 includes a step 302 of enriching the fibrillated tissue matrix. The enrichment of the fibrillated tissue matrix is accomplished by applying the biological constituent distillate to the fibrillated tissue matrix. In one embodiment, this includes soaking the fibrillated tissue matrix in the biological constituent distillate. In some embodiments, the combination is performed when the fibrillated tissue matrix is inside the pressure vessel. For example, the condenser and/or pump can reintroduce the biological constituent distillate back into the pressure vessel where the dehydrated, fibrillated tissue matrix is located. In another embodiment, the biological constituent distillate is collected and processed prior to usage. This can include allowing the biological constituent distillate to be analyzed for biological component levels, as well as further enhancement through additions of other components such as additional exosomes, cytokines, growth factors, sulfated proteoglycans, and other similar tissue components. Other products can also be added to the biological constituent distillate such as medicaments.

Next, the method includes a step 304 of dehydrating the enriched fibrillated tissue matrix. A fibrillated tissue matrix can be combined with the biological constituent distillate, and this resultant product can be dried. An example use of this enriched and dehydrated material includes embed the enriched and dehydrated fibrillated tissue matrix in an artificial thrombin to create a glue. Advantageously, this allows a coated (e.g., enriched) dried material to be suspended in the tissue sealant, and as that sealant is replaced, to free the growth factors within that have eluted and leaked into the underlying fibrillated tissue matrix.

In addition to adding components to the biological constituent distillate, the fibrillated tissue matrix can also be processed such as through the addition of fillers, medicaments, or exosomes, cytokines, growth factors, sulfated proteoglycans, and other similar tissue components. Thus, the method includes a step 306 of further enriching any of the enriched fibrillated matrix or the dehydrated fibrillated tissue matrix with any of a tissue growth enhancing product, a medicament, a filler, or any combinations thereof. This process can occur prior to or after step 304.

As noted above, the method can also include an optional step 308 of embedding the enriched and dehydrated fibrillated tissue matrix in an artificial thrombin to create a glue. This process can further include implanting the resultant product in a patient.

Figure 2:
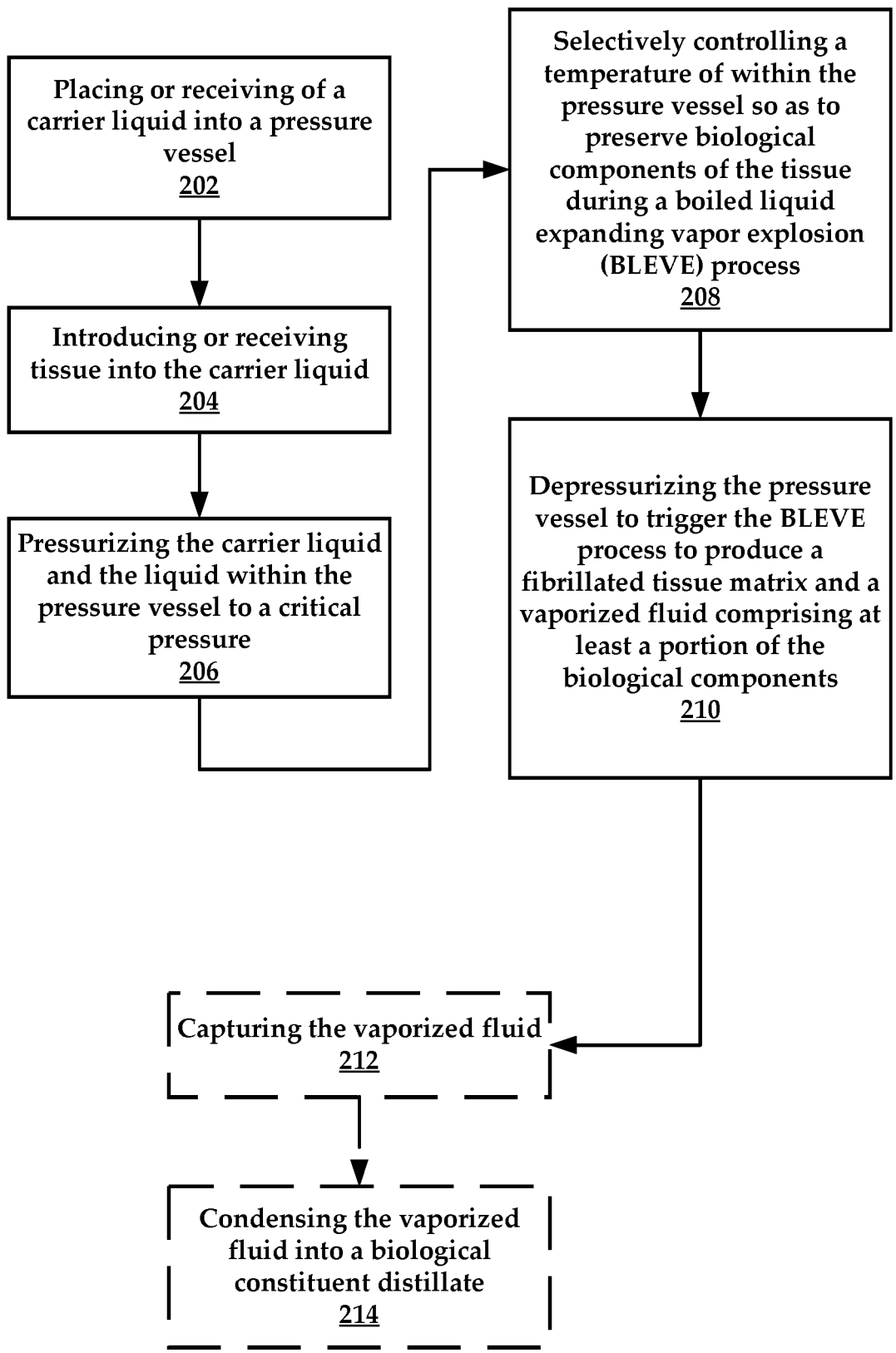
FIG. 2 is a flowchart of an example method of the present disclosure.
Figure 3:
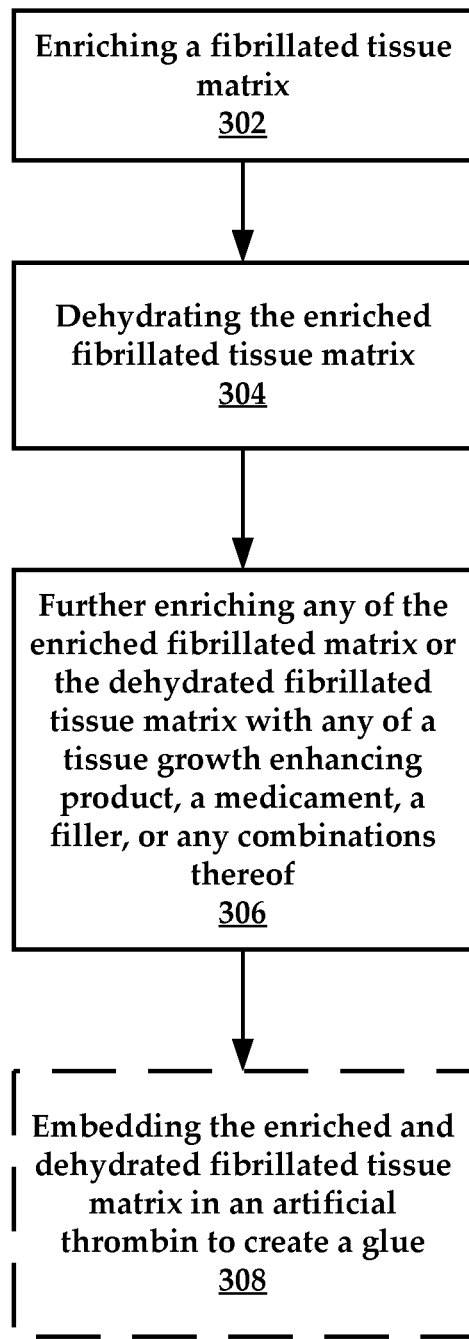
FIG. 3 is a flowchart of an example sub-method of the present disclosure that reflects the use of a fibrillated tissue matrix produced in the method of FIG. 2.
Figure 4:
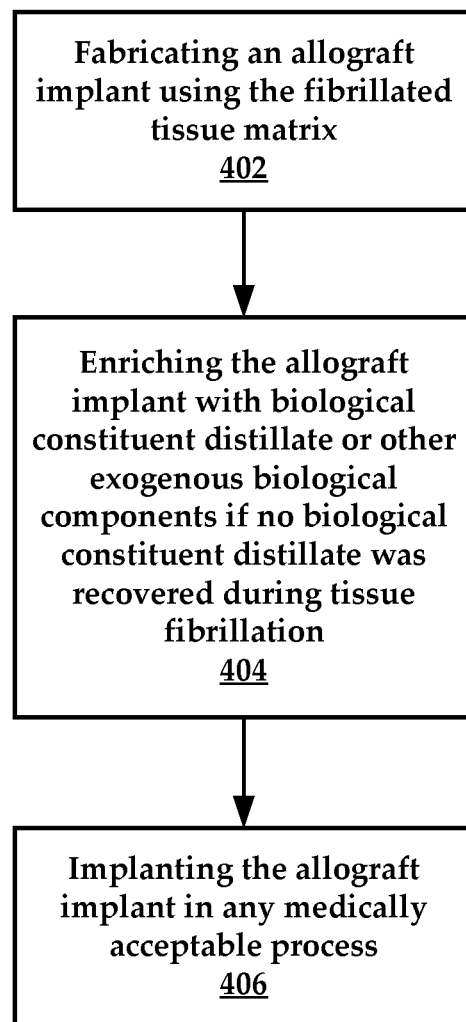
FIG. 4 is a flowchart of another example method of the present disclosure.

FIG. 4 is a flowchart of an example method of using a fibrillated tissue matrix of the present disclosure. In one example embodiment, the method includes a step 402 of fabricating an allograft implant using the fibrillated tissue matrix. This can include a dehydrated fibrillated tissue matrix or a rehydrated fibrillated tissue matrix. In some embodiments, this step occurs after either step 304 of FIG. 3, post rehydrating of the fibrillated tissue matrix, or after step 210 of FIG. 2, post creation of the fibrillated tissue matrix using a temperature controlled BLEVE process.

In various embodiments, the tissue used to create the fibrillated tissue matrix is obtained from a patient receiving the allograft implant such that the allograft implant is a chimeric graft that is cytokine autologous. This reduces the likelihood that the allograft implant will be rejected by the patient.

In some embodiments, the method includes a step 404 of enriching the allograft implant with biological constituent distillate or other exogenous biological components if no biological constituent distillate was recovered during tissue fibrillation. Next, the method includes a step 406 of implanting the allograft implant in any medically acceptable process. Again, this allograft implant can include a rehydrated (e.g., enriched) fibrillated tissue matrix.

Figure 5:
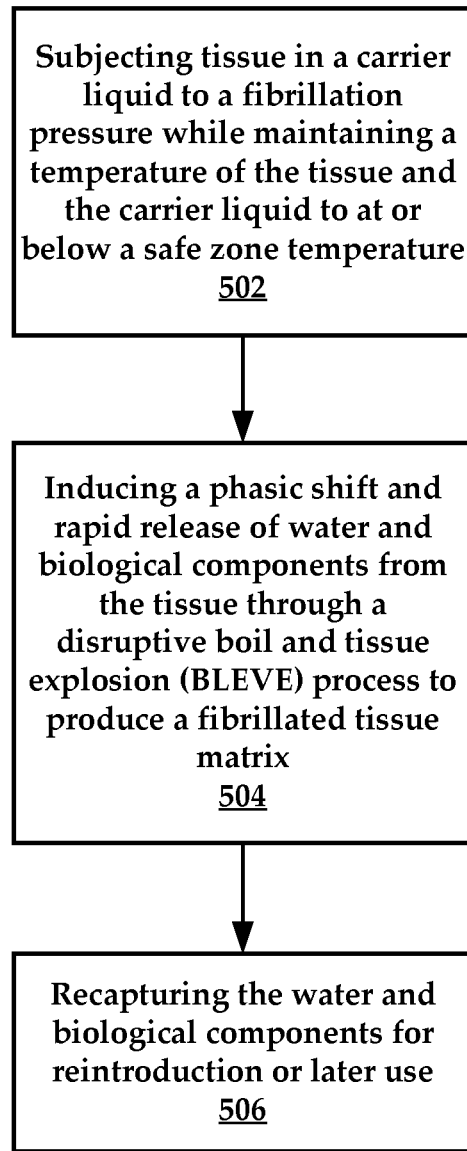
FIG. 5 is a flowchart of another example method of the present disclosure illustrating an optional allograft production process.

FIG. 5 is a flowchart of another example method of the present disclosure. The method includes a step 502 of subjecting tissue in a carrier liquid to a fibrillation pressure while maintaining a temperature of the tissue and the carrier liquid to at or below a safe zone temperature. In sum, the fibrillation pressure is a pressure sufficient to convert the tissue into a fibrillated matrix using BLEVE.

The method includes a step 504 of inducing a phasic shift and rapid release of water and biological components from the tissue through a disruptive boil and tissue explosion (BLEVE) process to produce a fibrillated tissue matrix. Next, the method includes a step 506 of recapturing the water and biological components for reintroduction or later use.

Figure 6:
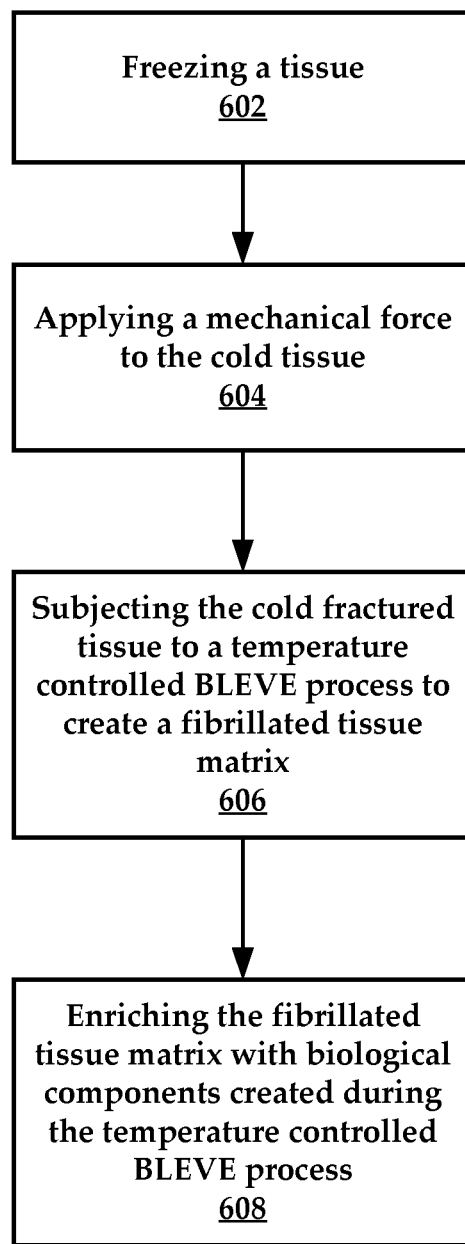
FIG. 6 is a flowchart of another example method of the present disclosure involving cold fracturing of a tissue.

FIG. 6 illustrates a flowchart of another example method of the present disclosure. This method in general includes freezing and blunt force impact to the tissue prior to BLEVE. For example, the method can include a step 602 of freezing a tissue. This can include subjecting the tissue to liquid nitrogen for a period of time. In general, this process includes reducing a temperature of the tissue to a fracturing temperature. The specific fracturing temperature is based on the tissue, as would be understood by one of ordinary skill in the art with the present disclosure before them. Once a desired temperature is reached, the method can include a step 604 of applying a mechanical force to the cold tissue, such as compression slamming of the cold tissue. This can include impacting the cold tissue with a hydraulic or other similar type of mechanical press to induce a fracturing of the cold tissue. The pressures used to facture the cold tissue depend on the mechanical properties of the cold tissue and/or the extent of fracturing desired. The method can also include a step 606 of subjecting the cold fractured tissue to a temperature controlled BLEVE process to create a fibrillated tissue matrix, as well as a step 608 of enriching the fibrillated tissue matrix with biological components created during the temperature controlled BLEVE process.

While this technology is susceptible of embodiment in many different forms, there is shown in the drawings and has been described in detail several specific embodiments with the understanding that the present disclosure is to be considered as an exemplification of the principles of the technology and is not intended to limit the technology to the embodiments illustrated.

Although the terms first, second, etc. may be used herein to describe various elements, components, regions, layers and/or sections, these elements, components, regions, layers and/or sections should not necessarily be limited by such terms. These terms are only used to distinguish one element, component, region, layer or section from another element, component, region, layer or section. Thus, a first element, component, region, layer or section discussed below could be termed a second element, component, region, layer or section without departing from the teachings of the present disclosure.

The terminology used herein is for the purpose of describing particular embodiments only and is not intended to be necessarily limiting of the disclosure. As used herein, the singular forms "a," "an" and "the" are intended to include the plural forms as well, unless the context clearly indicates otherwise. The terms "comprises," "includes" and/or "comprising," "including" when used in this specification, specify the presence of stated features, integers, steps, operations, elements, and/or components, but do not preclude the presence or addition of one or more other features, integers, steps, operations, elements, components, and/or groups thereof.

Example embodiments of the present disclosure are described herein with reference to illustrations of idealized embodiments (and intermediate structures) of the present disclosure. As such, variations from the shapes of the illustrations as a result, for example, of manufacturing techniques and/or tolerances, are to be expected. Thus, the example embodiments of the present disclosure should not be construed as necessarily limited to the particular shapes of regions illustrated herein, but are to include deviations in shapes that result, for example, from manufacturing.

Any and/or all elements, as disclosed herein, can be formed from a same, structurally continuous piece, such as being unitary, and/or be separately manufactured and/or connected, such as being an assembly and/or modules. Any and/or all elements, as disclosed herein, can be manufactured via any manufacturing processes, whether additive manufacturing, subtractive manufacturing and/or other any other types of manufacturing. For example, some manufacturing processes include three dimensional (3D) printing, laser cutting, computer numerical control (CNC) routing, milling, pressing, stamping, vacuum forming, hydroforming, injection molding, lithography and/or others.

Any and/or all elements, as disclosed herein, can include, whether partially and/or fully, a solid, including a metal, a mineral, a ceramic, an amorphous solid, such as glass, a glass ceramic, an organic solid, such as wood and/or a polymer, such as rubber, a composite material, a semiconductor, a nano-material, a biomaterial and/or any combinations thereof. Any and/or all elements, as disclosed herein, can include, whether partially and/or fully, a coating, including an informational coating, such as ink, an adhesive coating, a melt-adhesive coating, such as vacuum seal and/or heat seal, a release coating, such as tape liner, a low surface energy coating, an optical coating, such as for tint, color, hue, saturation, tone, shade, transparency, translucency, non-transparency, luminescence, anti-reflection and/or holographic, a photo-sensitive coating, an electronic and/or thermal property coating, such as for passivity, insulation, resistance or conduction, a magnetic coating, a water-resistant and/or waterproof coating, a scent coating and/or any combinations thereof.

Unless otherwise defined, all terms (including technical and scientific terms) used herein have the same meaning as commonly understood by one of ordinary skill in the art to which this disclosure belongs. The terms, such as those defined in commonly used dictionaries, should be interpreted as having a meaning that is consistent with their meaning in the context of the relevant art and should not be interpreted in an idealized and/or overly formal sense unless expressly so defined herein.

Furthermore, relative terms such as "below," "lower," "above," and "upper" may be used herein to describe one element's relationship to another element as illustrated in the accompanying drawings. Such relative terms are intended to encompass different orientations of illustrated technologies in addition to the orientation depicted in the accompanying drawings. For example, if a device in the accompanying drawings is turned over, then the elements described as being on the "lower" side of other elements would then be oriented on "upper" sides of the other elements. Similarly, if the device in one of the figures is turned over, elements described as "below" or "beneath" other elements would then be oriented "above" the other elements. Therefore, the example terms "below" and "lower" can, therefore, encompass both an orientation of above and below.

The description of the present disclosure has been presented for purposes of illustration and description, but is not intended to be exhaustive or limited to the present disclosure in the form disclosed. Many modifications and variations will be apparent to those of ordinary skill in the art without departing from the scope and spirit of the present disclosure. Exemplary embodiments were chosen and described in order to best explain the principles of the present disclosure and its practical application, and to enable others of ordinary skill in the art to understand the present disclosure for various embodiments with various modifications as are suited to the particular use contemplated.

While various embodiments have been described above, it should be understood that they have been presented by way of example only, and not limitation. The descriptions are not intended to limit the scope of the technology to the particular forms set forth herein. Thus, the breadth and scope of a preferred embodiment should not be limited by any of the above-described exemplary embodiments. It should be understood that the above description is illustrative and not restrictive. To the contrary, the present descriptions are intended to cover such alternatives, modifications, and equivalents as may be included within the spirit and scope of the technology as defined by the appended claims and otherwise appreciated by one of ordinary skill in the art. The scope of the technology should, therefore, be determined not with reference to the above description, but instead should be determined with reference to the appended claims along with their full scope of equivalents.

What is claimed is:

1. A system, comprising: a pressure vessel that can be selectively controlled with a control system relative to pressure and temperature to fibrillate a tissue disposed inside the pressure vessel, the tissue being disposed in a carrier fluid, the tissue being fibrillated using boiled liquid expanding vapor explosion (BLEVE) through pressurization of the pressure vessel and rapid decompression of the pressure vessel, the temperature within the pressure vessel being controlled so as to preserve biological components of the tissue during BLEVE, and reclaim for recombination and subsequent lyophyilization as an intact whole material in a form of a fibrillated tissue matrix that results from pressure modified processing with dehydration as a summative final difference, and a condenser configured to capture the vaporized fluid and condense the vaporized fluid into a biological constituent distillate.

2. The system according to claim 1, wherein the condenser is further configured to reintroduce a dehydrated version of the fibrillated tissue matrix with the biological constituent distillate to create an enriched fibrillated matrix.

3. The system according to claim 2, wherein the enriched fibrillated matrix is further enriched with any of a tissue growth enhancing product, a medicament, a filler, or any combinations thereof.

4. The system according to claim 1, wherein the fibrillated tissue matrix is configured as an allograft implant.

5. The system according to claim 4, wherein the tissue is obtained from a patient receiving the allograft implant such that the allograft implant is a chimeric graft that is cytokine autologous.

6. The system according to claim 1, wherein the controller is further configured to control the temperature to within a range of temperatures of approximately 35-41 degrees Centigrade, inclusive allowing for pyrogenic cytokines and their effective activity on cell shedding and reaction during BLEVE.

7. The system according to claim 1, wherein the controller is further configured to control the pressure within the pressure vessel to approximately 300-600 MPa, inclusive.

8. The system according to claim 1, wherein the controller is further configured to control the pressure within the pressure vessel to approximately 100-400 MPa, inclusive.

9. The system according to claim 1, further comprising a coiled tube heat exchanger in thermal contact with the pressure vessel, the controller controlling the coiled tube heat exchanger to maintain the temperature of the pressure vessel to between approximately zero and 100 degrees Centigrade, inclusive.

10. A system, comprising: a pressure vessel that can be selectively controlled with a control system relative to pressure and temperature to fibrillate a tissue disposed inside the pressure vessel, the tissue being disposed in a carrier fluid, the tissue being fibrillated using boiled liquid expanding vapor explosion (BLEVE) through pressurization of the pressure vessel and rapid decompression of the pressure vessel, the temperature within the pressure vessel being controlled so as to preserve biological components of the tissue during BLEVE, and reclaim for recombination and subsequent lyophyilization as an intact whole material in a form of a fibrillated tissue matrix that results from pressure modified processing with dehydration as a summative final difference, and a coiled tube heat exchanger in thermal contact with the pressure vessel, the controller controlling the coiled tube heat exchanger to maintain the temperature of the pressure vessel to between approximately zero and 100 degrees Centigrade, inclusive.

11. The system according to claim 10, further comprising a condenser configured to capture the vaporized fluid and condense the vaporized fluid into a biological constituent distillate, wherein the condenser is further configured to reintroduce a dehydrated version of the fibrillated tissue matrix with the biological constituent distillate to create an enriched fibrillated matrix.

12. The system according to claim 11, wherein the enriched fibrillated matrix is further enriched with any of a tissue growth enhancing product, a medicament, a filler, or any combinations thereof.

13. The system according to claim 10, wherein the fibrillated tissue matrix is configured as an allograft implant.

14. The system according to claim 13, wherein the tissue is obtained from a patient receiving the allograft implant such that the allograft implant is a chimeric graft that is cytokine autologous.

15. The system according to claim 10, wherein the controller is further configured to control the temperature to within a range of temperatures of approximately 35-41 degrees Centigrade, inclusive allowing for pyrogenic cytokines and their effective activity on cell shedding and reaction during BLEVE.

16. The system according to claim 10, wherein the controller is further configured to control the pressure within the pressure vessel to approximately 300-600 MPa, inclusive.

17. The system according to claim 10, wherein the controller is further configured to control the pressure within the pressure vessel to approximately 100-400 MPa, inclusive.

* * * * *